United States Patent [19]
Gumbrecht et al.

[11] Patent Number: 5,385,659
[45] Date of Patent: Jan. 31, 1995

[54] REFERENCE ELECTRODE

[75] Inventors: Walter Gumbrecht, Herzogenaurach; Wolfgang Schelter, Uttenreuth; Bernhard Montag, Forchheim, all of Germany

[73] Assignee: Siemens Aktiengesellschaft, Munich, Germany

[21] Appl. No.: 119,929

[22] Filed: Sep. 10, 1993

[30] Foreign Application Priority Data

Sep. 14, 1992 [DE] Germany .................... 4230691

[51] Int. Cl.⁶ ............................. G01N 27/26
[52] U.S. Cl. .................. 204/435; 204/416; 204/418; 204/415; 204/414
[58] Field of Search ............ 204/416, 418, 415, 414, 204/433, 435, 426

[56] References Cited

U.S. PATENT DOCUMENTS 4,874,500 10/1989 Madou et al. ............ 204/416
5,183,549 2/1993 Joseph et al. ............ 204/435

OTHER PUBLICATIONS

Viekkert, H. van den et al., "Solvent Polymeric Membranes Combined with Chemical Solid-State Sensors", *Analyst*, vol. 113 (1988), pp. 1029–1033.

Cammann, K., "Das Arbeiten mit ionenselektiven Elektroden", *Springer-Verlag* Berlin Heidelberg, N.Y. (1977), pp. 44–47.

J. Janata and R. H. Huber, "Solid State Chemical Sensors", *Academic Press Inc.*, Orlando (1985), pp. 101–103.

P. Bergveld and A. Sibbald, "Analytical and Biomedical Applications of Ion-selective Field-effect Transistors", *Elsevier Science Publishers B.V.*, Amsterdam (1988), pp. 63–74.

*Primary Examiner*—John Niebling
*Assistant Examiner*—Bruce F. Bell
*Attorney, Agent, or Firm*—Kenyon & Kenyon

[57] ABSTRACT

A planar reference electrode for chemical sensors, which are able to be supplied with a measuring fluid and a calibrating fluid. The planar reference electrode has the following components: an internal reference element situated on a flat substrate; a layer covering the substrate in the vicinity of the internal reference element and consisting of a structured polymer and having at least one trench, which serves as a diffusion channel and extends in the lateral direction from the internal reference element to a region that comes in contact with the measuring fluid or calibrating fluid to be supplied to the chemical sensor, where the diffusion in the diffusion channel is determined by the channel geometry and/or by a diffusion layer; and a covering which seals off the trench.

18 Claims, 2 Drawing Sheets

REFERENCE ELECTRODE

BACKGROUND OF THE INVENTION

1. Field of the Invention

The invention relates to a planar reference electrode for chemical sensors.

2. Description of Related Art

To measure ionic concentrations, for example ions such as $Na^+$, $K^+$ and $Ca^{2+}$, or pH-value, potentiometric measuring methods are preferably used at the present time. For this purpose, in addition to an ion-selective sensor, a reference electrode is required to supply a constant electric potential during the measuring operation. So-called electrodes of the second type are usually employed to this end, for example silver/silver-chloride electrodes (Ag/AgCl-electrodes).

The Ag/AgCl-electrode is comprised of a silver wire that has been coated with a silver-chloride layer and which dips into an electrolytic solution having a constant chloride ionic concentration. The electrolytic solution is thereby in electrical contact via a diaphragm, for example porous ceramics or glass grinding, with the measuring solution (c.f., for example: K. Cammann, *Das Arbeiten mit ionenselektiven Elektroden* [Working with Ion-Selective Electrodes], 2nd edition, Springer Verlag, Berlin, Heidelberg 1977, pp. 44–47).

A reference electrode having such a complex structure, however, is not compatible with ion sensors and pH sensors, such as ChemFETs (Chemically Sensitive Field Effect Transistors); c.f.: P. Bergveld and A. Sibbald, *Analytical and Biomedical Applications of Ion-Selective Field-Effect Transistors*, Elsevier Science Publishers B.V., Amsterdam 1988, pp. 63–74 (G. Svehla (publisher), *Comprehensive Analytical Chemistry*, volume XXIII). Therefore, it has been proposed to cover a common ISFET (Ion-Sensitive Field Effect Transistor) with a layer of an uncharged gel (c.f.: J. Janata in J. Janata and R. J. Huber (publisher), *Solid State Chemical Sensors*, Academic Press Inc., Orlando 1985, pp. 101–103). The effect of the gel is slowing down the ISFET response by lengthening the diffusion path. Because of the decelerated ion diffusion in the gel and given a rapid change (<1 min) from calibrating medium to measuring medium, the electric potential of the reference ChemFET remains constant for a short time (about 1 min) and can, thus, serve as a reference potential.

A further development of such a reference sensor is forming a hollow space across a pH-ISFET (pH-sensitive ISFET) situated on a silicon substrate. This hollow space is delimited by an anodically bonded glass layer (c.f.: *Analyst*, vol. 113 (1988), pp. 1029–1033), has a diameter of 500 $\mu$m and a height of 200 $\mu$m, and is filled with a hydrogel, i.e., a hydrophilic material. It may be that this pH-ISFET, which is "braked" with respect to response time, can—in combination with any ISFET—be used for a short time (change calibrating medium/measuring medium) as a reference sensor, but it is associated with some disadvantages. Thus, as far as manufacturing is concerned, its construction is coupled to the anodic bonding of a glass disk provided with holes on to a Si-wafer. On the one hand, this procedure is costly and, on the other hand, is not fully developed from a technological standpoint. Moreover, to achieve an adequate delay in the response characteristic of the "braked ChemFET" in such a configuration, very thick hydrogel layers must be applied to the ChemFET, namely layers having a thickness of about 200 $\mu$m (in a direction perpendicular to the extensional direction of the substrate).

SUMMARY OF THE INVENTION

Accordingly, it is an object of the invention to specify a planar reference electrode for chemical sensors, which is able to be supplied with a measuring fluid and a calibrating fluid, and which can be manufactured without entailing costly, disadvantageous technological steps, using cost-effective, standard technologies, and which does not require a thick diffusion layer.

This objective is attained in accordance with the invention by a reference electrode having the following features:

an internal reference element situated on a flat substrate;
a layer covering the substrate in the vicinity of the internal reference element and consisting of a structured polymer and having at least one trench, which serves as a diffusion channel and extends in the lateral direction from the internal reference element to a region that comes in contact with the measuring fluid, or rather calibrating fluid to be supplied to the chemical sensor, the diffusion in the diffusion channel being determined by the channel geometry and/or by a diffusion layer; and
a covering which seals off the trench.

BRIEF DESCRIPTION OF THE DRAWINGS

FIG. 1b is a top planar view of the reference electrode of FIG. 1a.

DETAILED DESCRIPTION OF THE INVENTION

Figure 1A:
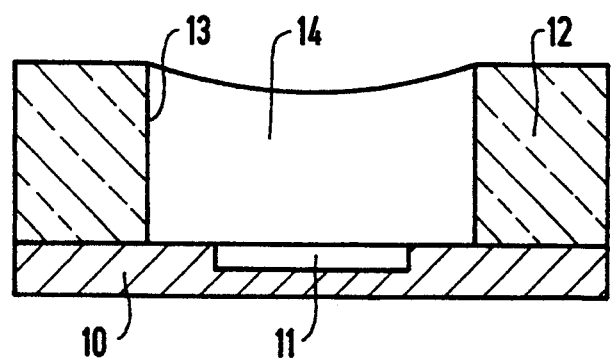
FIG. 1a is a cross-sectional view of a reference electrode of the prior art.

In the case of the reference electrode according to the invention, a silicon substrate, in particular a Si-wafer, is generally used as a substrate. Other materials also come under consideration, such as aluminum oxide and quartz. A so-called internal reference element, which can consist, for example, of noble metal, such as platinum, is situated on the substrate. However, the internal reference element is advantageously an ion sensor. An ion-sensitive electrode, such as a Ag/AgCl-electrode, can be used, in particular, as an ion sensor; however, an ISFET is preferably used for this purpose. The ISFET itself can be coated with Ag/AgCl, for example, and thus be $Cl^-$-sensitive; however, the ISFET is preferably pH-sensitive i.e., it is a pH-ISFET.

A polymer layer, which is generally 5 to 100 $\mu$m, preferably about 30 $\mu$m thick, is situated on the substrate. This polymer layer preferably consists of a polyimide, however, other polymer materials having structuring capability also come under consideration, such as polybenzoxazole. The polymer layer must be structured in the immediate vicinity of the internal reference element, to get a diffusion channel, i.e., an ionically conductive channel. Via this diffusion channel, the internal reference element is in contact—during operation of the sensor—with the fluid to be analyzed, i.e., the measuring solution, especially blood, or rather with a calibrating solution. Generally, the diffusion channel has—altogether—a height of a few μm, a width of a few 10 μm, and a length of a few 100 μm.

The diffusion channel can consist of a single, relatively wide trench or of several relatively narrow trenches, which run parallel to one another and are separated from one another by segments. These trenches, which are formed by structuring of the polymer-layer, have a covering which seals them off. This can be a rigid convering, which is bonded to the polymer layer and, in some instances, to the diffusion layer. Preferably, however, a seal is used, i.e., an elastic sealing material, in particular an O-ring. This type of structure makes it possible for the contact area between the solution and the sensor to lie far enough away from the internal reference element, namely by a few 100 μm. In this manner, after a change has taken place from the calibrating solution to the measuring solution, the diffusion of ions of the measuring solutions to the internal reference element takes place only laterally and, and as result, slowly enough. Thus, when an ISFET is used as an internal reference element, any high electrical resistance existing between the reference electrode and the sensor does not have a negative effect.

In addition to the channel geometry, a diffusion layer can also be used to adjust the diffusion in the diffusion channel. The diffusion layer preferably consists of an electrolytic solution (calibrating solution), but can also be a hydrogel, which is swollen with electrolytic solution in the operating state. Polymeric 2-hydroxyethylmethacrylate (pHEMA) is especially suited as a hydrogel. To prepare such a diffusion layer, the trenches of the polymer structure are filled with the hydrogel. A preferred diffusion layer can be realized by filling the trenches with a water-soluble polymer, such as polyvinylpyrrolidone (PVP). After initial operation, this polymer is then dissolved by the calibrating solution and replaced in this manner by electrolytic solution. Thus, a free diffusion is guaranteed in the diffusion channel, i.e., pure diffusion potentials exist, and no disturbing membrane potentials, such as Donnan-potentials.

Figure 1B:
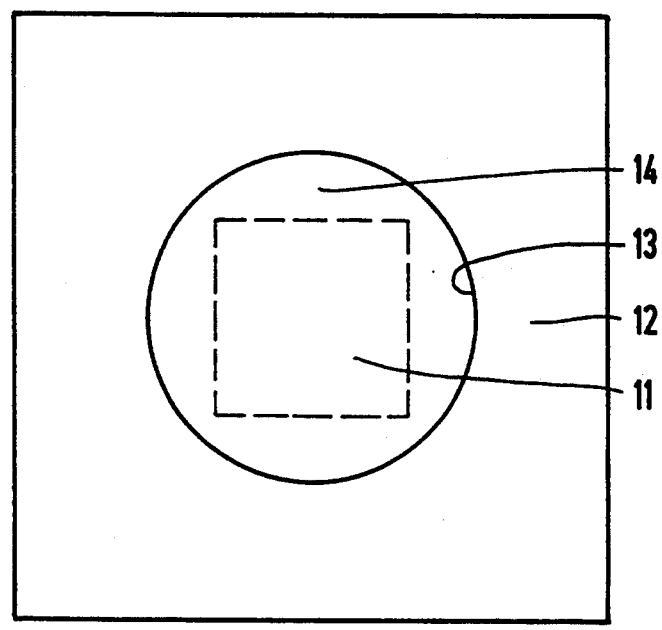

The invention will be clarified in greater detail on the basis of the following specific comparative example. In the case of the known reference electrode of the prior art shown in FIG. 1, and ISFET 11 is situated on the surface of a silicon substrate 10. The silicon substrate 10 is provided with a layer 12 of glass. The glass layer 12 has a hole 13 in the region of the ISFET 11. The hole 13 is filled with a hydrogel 14, which represents a diffusion layer.

Figure 2A:
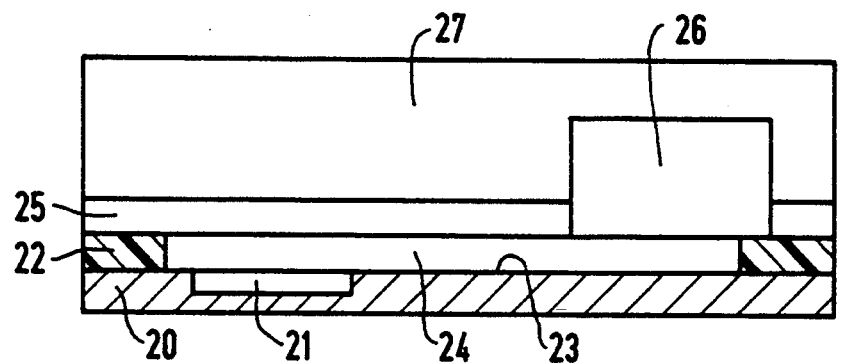
FIG. 2a is a cross-sectional view of a reference electrode in accordance with the invention.
Figure 2B:
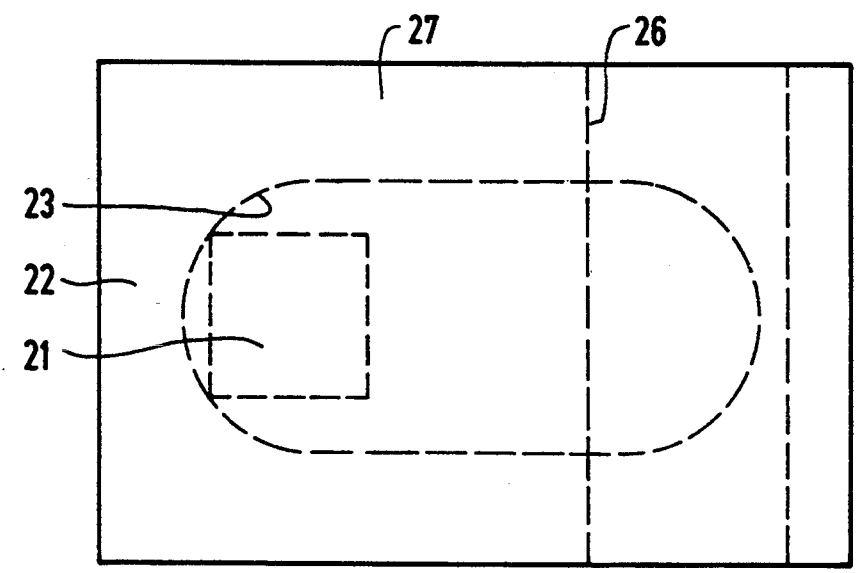
FIG. 2b is a top planar view of the reference electrode of FIG. 2b.

A preferred specific embodiment of the reference electrode according to the invention is illustrated in FIG. 2. An internal reference element 21, in particular an ISFET, preferably a pH-ISFET, is arranged on a flat substrate 20, in particular a silicon substrate. The substrate 20 is provided with a layer 22 of a polymer, in particular of polyimide, in the area of the internal reference element 21. The polymer layer 22 is structured and has a trench 23, which serves as a diffusion channel. For this purpose, the trench 23 is filled with a water-soluble polymer 24, such as polyvinylpyrrolidone, and provided with a covering 25 that seals it off. The trench 23 extends in the lateral direction, i.e., parallel to the surface of the substrate 20, and represents a connection between the internal reference element 21 and a flow-through channel 26, which leads to a chemical sensor—not shown in the Figure. The flow-through channel 26 is essentially formed by a cut-out in a housing 27.

What is claimed is:

1. A planar reference electrode for chemical sensors, which are able to be supplied with a measuring fluid and a calibrating fluid, comprising:
   an internal reference element situated on a flat substrate;
   a structured polymer layer covering the substrate in a vicinity of the internal reference element, the structured polymer layer having at least one trench, which serves as a diffusion channel and which extends in a lateral direction from the internal reference element to a region in contact with a measuring fluid to be supplied to the chemical sensor, where diffusion characteristics in the trench are determined, at least in part, by the trench geometry; and
   a covering which seals off the trench.

2. The planar reference electrode according to claim 1 further comprising a diffusion layer disposed in the trench for determining, at least in part, diffusion characteristics in the trench.

3. The planar reference electrode according to claim 1 wherein the internal reference element is an ion sensor.

4. The planar reference electrode according to claim 2 wherein the internal reference element is an ion sensor.

5. The planar reference electrode according to claim 3 wherein the ion sensor is an ISFET.

6. The planar reference electrode according to claim 4 wherein the ion sensor is an ISFET.

7. The planar reference electrode according to claim 5 wherein the ion sensor is a pH-ISFET.

8. The planar reference electrode according to claim 1 wherein the polymer layer is from 5 to 100 μm thick.

9. The planar reference electrode according to claim 2 wherein the polymer layer is from 5 to 100 μm thick.

10. The planar reference electrode according to claim 3 wherein the polymer layer is from 5 to 100 μm thick.

11. The planar reference electrode according to claim 4 wherein the polymer layer is from 5 to 100 μm thick.

12. The planar reference electrode according to claim 8 wherein the polymer layer is about 30 μm thick.

13. The planar reference electrode according to claim 1 wherein the polymer layer is a polyimide.

14. The planar reference electrode according to claim 2 wherein the polymer layer is a polyimide.

15. The planar reference electrode according to claim 1 wherein the trench is covered by a seal.

16. The planar reference electrode according to claim 2 wherein the trench is covered by a seal.

17. The planar reference electrode according to claim 2 wherein the diffusion layer is a water-soluble polymer which is filled in the trench.

18. The planar reference electrode according to claim 17 wherein the water-soluble polymer is polyvinylpyrrolidone.

* * * * *